US009016110B2

(12) United States Patent
Seifert et al.

(10) Patent No.: US 9,016,110 B2
(45) Date of Patent: Apr. 28, 2015

(54) APPARATUS FOR ON-LINE CONTINUOUS CHLORINE ANALYSIS IN TURBID WATER AND PROCESS STREAMS

(75) Inventors: Martin Seifert, Mayen (DE); Peter Enskat, Kelsterbach (DE); Bernd Schreiner, Niedernberg (DE); Stephen B. Ashton, Saint Charles, IL (US)

(73) Assignee: Nalco Company, Naperville, IL (US)

( * ) Notice: Subject to any disclaimer, the term of this patent is extended or adjusted under 35 U.S.C. 154(b) by 29 days.

(21) Appl. No.: 12/951,179

(22) Filed: Nov. 22, 2010
(Under 37 CFR 1.47)

(65) Prior Publication Data

US 2012/0125079 A1    May 24, 2012

(51) Int. Cl.
*G01N 33/18*    (2006.01)

(52) U.S. Cl.
CPC .................................. *G01N 33/18* (2013.01)

(58) Field of Classification Search
USPC ........................................................ 73/61.43
See application file for complete search history.

(56) References Cited

U.S. PATENT DOCUMENTS

| 3,464,557 | A | * | 9/1969 | Fowler | 210/97 |
| 3,654,801 | A | * | 4/1972 | Keefer et al. | 73/28.04 |
| 3,697,227 | A | * | 10/1972 | Agnew et al. | 422/409 |
| 3,706,378 | A | * | 12/1972 | Markwick | 210/107 |
| 4,389,879 | A | * | 6/1983 | Bach et al. | 73/61.73 |
| 4,818,413 | A | * | 4/1989 | Hoover et al. | 210/739 |
| 5,000,006 | A | * | 3/1991 | Itoh et al. | 62/635 |
| 5,104,527 | A | * | 4/1992 | Clinkenbeard | 210/94 |
| 5,324,665 | A |   | 6/1994 | Lessard | |
| 2005/0276724 | A1 | * | 12/2005 | Bremauer | 422/29 |
| 2008/0116144 | A1 |   | 5/2008 | Vineyard et al. | |
| 2009/0242469 | A1 |   | 10/2009 | Calabrese | |
| 2011/0024338 | A1 | * | 2/2011 | Milani | 210/96.1 |

FOREIGN PATENT DOCUMENTS

| CN | 101406773 | 4/2009 |
| CN | 101477843 | 7/2009 |
| JP | 2111496 A | 4/1990 |

(Continued)

OTHER PUBLICATIONS

HACH CL17 User Manual, Sep. 2011, Edition 7.*

*Primary Examiner* — Peter Macchiarolo
*Assistant Examiner* — Nathaniel Kolb
(74) *Attorney, Agent, or Firm* — Benjamin Carlsen

(57) ABSTRACT

The invention is directed towards methods and apparatus for accurately detecting the presence and concentration of an oxidant in a turbid water sample. This method is very helpful in allowing accurate and efficient (not too much nor too little) amounts of microbe killing oxidants to be introduced to water supplies that require oxidants but which at present cannot be measured properly. The method comprises the steps of: passing the water through at least one filter array, passing the filtered water to an analyzer, and then returning from the analyzer a measurement of the concentration. The filter array comprises at least one filter constructed and arranged to remove turbidity inducing material but not oxidant from the water sample. The analyzer can be a commonly commercially available analyzer that currently cannot accurately measure the oxidant concentration if the water had not been so filtered. This method allows users to apply easily available oxidant measuring technology to applications such as paper mill water where it is needed but was previously was not applicable.

11 Claims, 1 Drawing Sheet

(56) References Cited

FOREIGN PATENT DOCUMENTS

| | | |
|---|---|---|
| JP | 2001083095 | 3/2001 |
| JP | 2003200007 | 7/2003 |
| JP | 2003302392 | 10/2003 |
| JP | 20043544147 A | 12/2004 |
| KR | 2005063259 | 6/2005 |

* cited by examiner

APPARATUS FOR ON-LINE CONTINUOUS CHLORINE ANALYSIS IN TURBID WATER AND PROCESS STREAMS

CROSS-REFERENCE TO RELATED APPLICATIONS

Not Applicable.

STATEMENT REGARDING FEDERALLY SPONSORED RESEARCH DEVELOPMENT

Not Applicable.

BACKGROUND OF THE INVENTION

The present invention relates generally to methods of, and apparatus for accurately monitoring the amount of biocides and particular oxidants present in a given water volume. Oxidants such as sodium hypochlorite and other halogen-based compositions (including but not limited to Actibrom, BCDMH, and Stabrex) are frequently used to control the growth of microbial organisms and. other biological deposit formations in water and industrial processes. Efficient and effective use of these compositions however requires that proper concentrations be maintained. This is best achieved by use of an online system that provides real time up to date concentration information.

One on-line method of monitoring the concentrations in water involves determining the amount of total halogen and free halogen residuals. This can be accomplished by a number of commercially available devices using various techniques. The HACH CL17 measures free and total chlorine using colorimetric method and N,N-diethyl-p-phenylenediamine (DPD) indicator reagent. Unfortunately, the use of such colorimetric and indicator reagents is limited to water systems with low solids and with turbidity values below 5 nephelometric turbidity units (NTU). Paper process water typically has a solids content ranging from 0.1 to 0.5% even in the most clarified parts of the process, which greatly exceeds the limitations of available technology.

Another method is Oxidation-Reduction Potential (ORP). ORP however only gives an indirect measurement of oxidant concentration. Also because ORP is affected by factors other than just halogen concentration. under certain circumstances, and in particular in highly turbid environments it is inaccurate.

Yet another method is Amperometric measurements. Amperometric measurements use a conductive element sensor (typically having a copper and platinum or gold electrode). A small amount of potential is applied to the sensor electrodes. An electric charge is then generated by the chemical reduction of the oxidant. The resulting charge is in direct linear proportion to the amount of residual halogen present in the sample. Amperometric measurements however require membrane caps, which rapidly become fouled when continuously used in many industrial processes. As a result, Amperometric measurements are only of limited practical use.

It is therefore useful and desirable to provide methods and apparatus to better detect the concentration of oxidants in water samples. The art described in this section is not intended to constitute an admission that any patent, publication or other information referred to herein is "Prior Art" with respect to this invention, unless specifically designated as such. In addition, this section should not be construed to mean that a search has been made or that no other pertinent information as defined in 37 CFR §1.56(a) exists.

BRIEF SUMMARY OF THE INVENTION

At least one embodiment of the invention is directed to a method of accurately detecting the presence and concentration of an oxidant in a turbid water sample, the method comprising the steps of: 1) passing the water through a filter array, the filter array comprises at least one filter constructed. and arranged to remove turbidity inducing material but not oxidant from the water sample, 2) then passing the filter array filtered water to an oxidant monitor that would not be able to accurately measure the oxidant concentration if the water had not been so filtered, and 3) returning from the monitor a measurement of the concentration.

The filter array may comprise at least two filters, the filters in series with each other relative to the downstream flow of the water. At least one less-downstream filter may be constructed and arranged to filter larger and coarser turbidity inducing material than at least one more-downstream filter. The filter array may comprise a filter-band type filter. The filter array may comprise a filter, which is constructed and arranged to rotate, the rotation preventing the accumulation and plugging of the filter by continuous contact with turbidity inducing material.

The oxidant may be halogen based and may be sodium hypochlorite. The monitor may determine the oxidant concentration by using an algorithm relying upon determining the amount of total halogen and free halogen residuals. The flow rate through the filter array may be adjusted by diverting some of the water into a side spillway so the remaining sample flow is compatible with the time interval needed by the monitor to measure the concentration.

The method may further comprise the step of intermittently passing high concentrations of oxidant to the monitor where the monitor is constructed and arranged to thereafter not indicate that the measured oxidant amounts are measured oxidant amounts until one item has occurred selected from the list consisting of: the measured oxidant concentration is no greater than 0-40% of the measured amount before the high concentration was passed through, a predetermined time has passed, a predetermined multiple of the time interval of the analyzer has passed, and any combination thereof. The high concentrations of oxidant may reduce fouling of at least one item selected from the monitor, the pumps, the hoses, and any combination thereof. The water sample may be water from a paper mill process stream. The turbidity inducing material may be selected from the list consisting of: cellulose fibers, mineral fillers, property enhancing polymers, sizing agents, wood chips, and any combination thereof.

Additional features and advantages are described herein, and will be apparent from, the following Detailed Description.

BRIEF DESCRIPTION OF THE DRAWINGS

A detailed description of the invention is hereafter described with specific reference being made to the drawings in which.

DETAILED DESCRIPTION OF THE INVENTION

Figure 1:
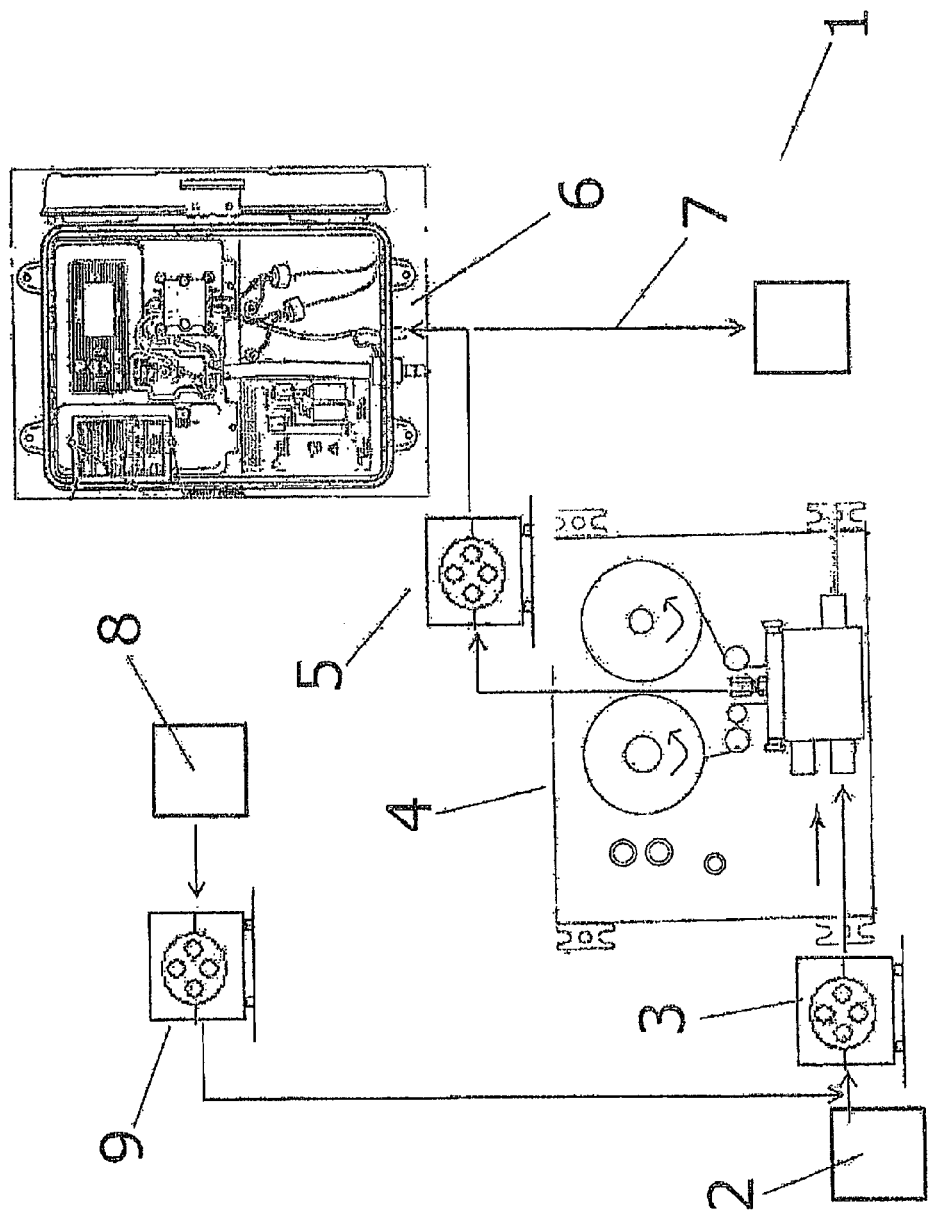
FIGURE 1 is a schematic drawing of the analyzer system.

For purposes of this application the definition of these terms is as follows:

"Fouling" means the undesirable presence of or deposition of any organic or inorganic material in the water or on a surface.

"Monitor" means a device constructed and arranged to measure at least one physical or chemical characteristic and to output a signal or display in response to that measurement.

In the event that the above definitions or a description stated elsewhere in this application is inconsistent with a meaning (explicit or implicit) which is commonly used, in a dictionary, or stated in a source incorporated by reference into this application, the application and the claim terms in particular are understood to be construed according to the definition or description in this application, and not according to the common definition, dictionary definition, or the definition that was incorporated by reference. In light of the above, in the event that a term can only be understood if it is construed by a dictionary, if the term is defined by the *Kirk-Othmer Encyclopedia of Chemical Technology*, 5th Edition, (2005), (Published by Wiley, John & Sons, Inc.) this definition shall control how the term is to be defined in the claims.

Referring now to FIGURE 1 it is shown that at least one embodiment is a method and apparatus (1) for accurately determining the amount of oxidant in a volume of water. The water flows from a source (2) and undergoes multiple pre-filtering processes prior to analysis by a prior art oxidant analyzer or a "doctrine of equivalents" equivalent. The pre-filtering is accomplished by passing the water through a filter array (4). The water may flow under due to the effects of one or more pumps (3). The pre-filtering removes materials that would otherwise foul the analyzer (6) or which would render the measurement inaccurate. At the same time the pre-filtering is done in a manner that does not alter the oxidant content of a sample so the oxidant sample is truly representative or the water volume being analyzed.

In at least one embodiment the water source is a volume of process water from a paper mill. Such process water is typically highly turbid and contains large amounts of cellulose and other fibers, paper and wood solids, fillers, minerals, and various property enhancing additives, all of which overwhelm and make impossible accurate and/or long term analysis of the oxidant content of the process water. This in turn makes the addition of oxidants "blind" and is therefore either too much and needlessly wasteful (and possibly toxic) or too little and not sufficiently effective.

In at least one embodiment the pre-filtration is accomplished by the use of one or more bandfilters. Band filters are known in the art as a filter apparatus that allows the liquid to always pass through a clean filtering material. This cleanliness is achieved because the band itself is a long strip that is constantly pulled (much like the tape in a cassette tape) across an aperture through which the liquid flows. Because it is pulled, the same given filtering surface is only in contact with the liquid for a short period of time and does not have time for significant fouling to occur. Commonly bandfilters are at least in part held in place against the aperture by a pressure gradient pulling the hand in the same direction as the liquid flow. In at least one embodiment this gradient is caused by a pump (5) downstream from the filter (4). Often the band is in a loop that includes a cleaning stage the same section of band will cycle past the aperture again and again, but because it is constantly cleaned, the effect is a perpetually clean filter surface through which the liquid flows.

In at least one embodiment a bandfilter passes the aperture at a rate of between 0.5 1 cm per minute to 1 1 cm per hour. In at least one embodiment the bandfilter is constructed and arranged to be used with liquids In at least one embodiment, the liquids that pass through the bandfilter do not exceed 2% (meaning 2% fibers and most/all of the remaining 98% is water). In at least one embodiment the bandfilter is rotated and is continuously washed so turbidity-inducing materials do not clog up the filter.

In at least one embodiment there is only one filter. In at least one embodiment two or more filters are positioned in series with each other relative to the flow path of the water. The multiple serially positioned filters remove ever-increasing proportions of the turbidity inducing materials from the water sample.

In at least one embodiment the filters are so effective at reducing the effects of turbidity inducing materials that process waters having a solids content as high at 6% can effectively be measured. In at least one embodiment the one or more filters are arranged to remove the turbidity inducing materials from a sample that is from 2-4% solids.

In at least one embodiment the analyzer (6) downstream from the filters is a HACH CL17 analyzer.

In at least one embodiment the flow rate of the water samples through the one or more filters are constructed and arranged to match the optimal flow rate for the analyzer. For example in the HACH CL17, the analyzer measures residuals at 3-minute intervals and the flow rate is adjusted to accommodate that rate. In at least One embodiment if the flow rate of the water samples exceeds the measuring rate of the analyzer, a portion of the water sample is diverted down a spillway (7) and the remainder is the optimal amount which is passed on to the analyzer. In this way allow rate that is greater than the interval rate of the analyzer can provide accurate readings. In at least one embodiment the spillway is constructed and arranged to always assure that liquid passes into the analyzer at a fixed rate.

In at least one embodiment a cleaning cycle is available to the system. The cleaning cycle allows one or more of the sensor, hoses, pumps, filters, etc . . . to be maintained in a clean state. As various parts of the system continuously receive potentially infested water, microbial slimes may accumulate along various surfaces that contact with this infested water. In at least one embodiment the cleaning cycle can be achieved by diverting the process flow water away from one or more portions of the system and instead introducing a liquid stream that is highly concentrated with oxidant or other biocide.

In at least one embodiment concentrated sodium hypochlorite (or another oxidant or biocide) is introduced to at least one portion of the system and it cleans that portion. In at least one embodiment, concentrated sodium hypochlorite (or another oxidant or biocide) is introduced to at least one portion of the system, and the introduced sodium hypochlorite (or another oxidant or biocide) continues on to subsequent downstream portions of the system and cleans those downstream portions. This allows one insertion of a chemical to accomplish effective cleaning of multiple portions of the system. In at least one embodiment the concentrated sodium hypochlorite (or another oxidant or biocide) is introduced into a process stream which is upstream of at least one of the pre-filtering steps. In at least one embodiment the sodium hypochlorite (or another oxidant or biocide) (8) is introduced by its own pump (9).

In at least one embodiment the sample water pump (3), post filter pump (5), and the cleaning cycle pump (9) are coordinated to run at the same time with different flow rates. In at least one embodiment the sample water pump (3) runs at a flow rate of between 75 to 250 times as great as the post filter pump (5). In at least one embodiment the cleaning cycle pump (9) runs at a flow rate of between $3*10^{-7}$ to $6*10^{-7}$ times more slowly than the sample water pump (3). In an exemplary embodiment the sample water pump (3) runs at a rate of 1 liter per minute, the post filter pump (5) runs at 5-10 ml per minute, and the cleaning cycle pump (9) runs at a rate of 30 ml per 12 hours.

Even after this slime-removing stream is no longer flowing through the sensor, much higher oxidant concentrations may persist for a while. In at least one embodiment the sensor (or process control equipment that is in communication with the sensor) is designed to reject as inaccurate oxidant readings until after either a time interval which is a multiple of the time interval of the sensor or until the detected oxidant levels are back down to close to what they were (for example within 0%-50% of what they were) before the cleaning cycle was initiated. In at least one embodiment the time interval is between 1 and 7 minutes long.

At least one possible example of the cleaning process is as follows: The cleaning cycle pump (9) pumps hypochlorite (and/or another oxidant or biocide) to clean some or all of the hoses and the analyzer (6). As a result the analyzer detects chlorine levels are higher than typical (for example >5 ppm). After a communication with the process control system for the apparatus (1), the apparatus switches into a static state for an interval of time (for example: 30 minutes). After the time interval has lapsed, the process control system returns the apparatus back to a regular state.

While this invention may be embodied in many different forms, there described in detail herein specific preferred embodiments of the invention. The present disclosure is an exemplification of the principles of the invention and is not intended to limit the invention to the particular embodiments illustrated. All patents, patent applications, scientific papers, and any other referenced materials mentioned herein are incorporated by reference in their entirety. Furthermore, the invention encompasses any possible combination of some or all of the various embodiments described herein and incorporated herein.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

All ranges and parameters disclosed herein are understood to encompass any and all subranges subsumed therein, and every number between the endpoints. For example, a stated range of "1 to 10" should be considered to include any and all subranges between (and inclusive of) the minimum value of 1 and the maximum value of 10; that is, all subranges beginning with a minimum value of 1 or more, (e.g. 1 to 6.1), and ending with a maximum value of 10 or less, (e.g. 2.3 to 9.4, 3 to 8, 4 to 7), and finally to each number 1, 2, 3, 4, 5, 6, 7, 8, 9, and 10 contained within the range.

This completes the description of the preferred and alternate embodiments of the invention. Those skilled in the art may recognize other equivalents to the specific embodiment described herein which equivalents are intended to be encompassed by the claims attached hereto.

What is claimed is:

1. A method of accurately detecting the presence and concentration of an oxidant in a turbid water sample of a process water stream, the method comprising the steps of:

passing the water sample through a filter array, the filter array comprises at least one filter which is a filter-band type filter comprising a first rotating wheel and a second rotating wheel around both of which a water permeable tape is wound, the wheels are constructed and arranged to rotate in the same direction and thereby the tape is unwound from the first wheel and further wound around the second wheel and the tape is washed to remove turbidity inducing material so that turbidity inducing material does not clog up the tape, the tape being washed such that before the tape is unwound from the first wheel it is essentially clean and this essentially clean tape is what the water passes through so the water only passes through an essentially clean tape, wherein the tape is permeable such that it can remove turbidity inducing material but not oxidant from the water sample, the filter is constructed and arranged to rotate and thereby prevent the accumulation and plugging of the filter by continuous contact with turbidity inducing material, then passing the filter array filtered water to an oxidant monitor that would not be able to accurately measure the oxidant concentration if the water had not been so filtered, wherein the oxidant monitor measures oxidant levels using N,N-diethyl-p phenylenediamine indicator reagent, holding, at least in part, the filter-band type filter in place by a pressure gradient caused by a pump, the pressure gradient configured for pulling the tape in a direction of water sample flow from the filter array to the oxidant monitor, and returning from the monitor a measurement of the concentration, the monitor continuously measuring the concentration of an oxidant from the process water stream.

2. The method of claim 1 wherein the filter array comprises at least two filters, the filters in series with each other relative to the downstream flow of the water.

3. The method of claim 2 wherein at least one less-downstream filter is constructed and arranged to filter larger and coarser turbidity inducing material than at least one more-downstream filter.

4. The method of claim 1 in which the oxidant is halogen based.

5. The method of claim 1 in which the oxidant is sodium hypochlorite.

6. The method of claim 1 in which the monitor determines the oxidant concentration by using an algorithm relying upon determining the amount of total halogen and free halogen residuals.

7. The method of claim 1 in which the flow rate through the filter array is adjusted by diverting some of the water into a side spillway so the remaining sample flow is compatible with the time interval needed by the monitor to measure the concentration.

8. The method or claim 1 further comprising the step of intermittently passing high concentrations of oxidant to the monitor, the monitor constructed and arranged to thereafter not indicate that the measured oxidant amounts are measured oxidant amounts until one item has occurred selected from the list consisting of: the measured oxidant concentration is no greater than 0-20% of the measured amount before the high concentration was passed through, a predetermined time has passed, a predetermined multiple of the time interval of the analyzer has passed, and any combination thereof.

9. The method of claim 8 in which the high concentrations of oxidant reduce fouling of at least one item selected from the monitor, the pumps, the hoses, and any combination thereof.

10. The method of claim 1 in which the water sample is water from a paper mill process stream.

11. The method of claim 1 in which the turbidity inducing material is selected from the list consisting on cellulose fibers, mineral fillers, property enhancing polymers, sizing agents, wood chips, and any combination thereof.

\* \* \* \* \*